United States Patent [19]
Cohen et al.

[11] Patent Number: 5,069,906
[45] Date of Patent: Dec. 3, 1991

[54] INTRA-VAGINAL DEVICE AND METHOD

[75] Inventors: Robert S. Cohen, New York, N.Y.; James M. Pierce; William H. Kinsey, both of Coral Gables, Fla.

[73] Assignee: MaxiMed Corporation, New York, N.Y.

[21] Appl. No.: 625,808

[22] Filed: Dec. 11, 1990

Related U.S. Application Data

[63] Continuation of Ser. No. 257,156, Oct. 14, 1988, Pat. No. 4,983,393, which is a continuation of Ser. No. 57,898, Jul. 21, 1987, abandoned.

[51] Int. Cl.$^5$ ................................................ A61K 9/02
[52] U.S. Cl. .................................... 424/430; 424/426; 424/431; 424/432; 424/433
[58] Field of Search ................. 424/430, 431, 432, 433

[56] References Cited

U.S. PATENT DOCUMENTS 3,493,652  2/1970  Hartman .......................... 424/433
4,381,772  5/1983  Guistini et al. ................. 128/132 R
4,707,362  11/1987  Nuwayser ......................... 424/433

Primary Examiner—Thurman K. Page
Assistant Examiner—James Spear
Attorney, Agent, or Firm—Cooper & Dunham

[57] ABSTRACT

The invention disclosed provides an intra-vaginal device prepared using ingredients which slowly release in the vagina over a significant period of time. The present intra-vaginal device also usefully serves as a drug release means for controllably releasing a drug in the vagina. A method for controlled drug release in the vagina is also disclosed.

2 Claims, 1 Drawing Sheet

INTRA-VAGINAL DEVICE AND METHOD

This is a continuation of application Ser. No. 257,156, filed Oct. 14, 1988, now U.S. Pat. No. 4,983,393 which, in turn, is a continuation of Ser. No. 057,898 filed Jul. 21, 1987, abandoned.

BACKGROUND OF THE INVENTION

1. Field of the Invention

The present invention relates to an improved intra-vaginal device, and more particularly to such a device including drugs which may be controllably released in the vagina over a sustained period of time. The present invention also provides a new improved drug release method using the presently discovered intra-vaginal drug delivery system.

2. Description of the Prior Art

As an intravaginal contraceptive barrier, the diaphragm, usually prepared from a sift rubber cup with a reinforced rim that is inserted into the vagina to block access of sperm to the cervix, is an excellent alternative for women who has conditions which do not allow the use of oral contraceptives or intra-uterine-device (IUD) or who do not wish to use these method. Although the diaphragm is usually 100% risk-free and can be a reliable contraceptive for most women, to be effective it must be used properly. Also, each individual must be specially fitted with such a contraceptive barrier thereby limiting any size standardization.

Many factors associated with the use of presently available diaphragms have prevented their widespread use. While the diaphragm acts as a barrier to most sperm, it is not normally held tightly enough in front of the cervix to prevent entirely the passage of all sperm around the rim. Therefore, the device is used in most instances with a spermicidal cream or jelly. The vaginal spermicides are often messy and tend to flow our of the vagina. Replenishing the spermicide can be expensive if the diaphragm is used frequently.

The use of conventional diaphragms not only interrupts normal sexual intercourse, but also it presents problems with maintenance associated with diaphragm washing, sterilization, drying, powdering, and inspection prior to insertion on reuse.

Numerous contraceptive devices have been developed to eliminate the disadvantages of current reusable diaphragms. Prior art annular devices provide controlled release of surfactant-type spermicides in the vagina, but do not act as a barrier to sperm deposition on or in the area of the cervix. Devices with compartments that substantially cap or block the cervix and provide controlled release of spermicidal surfactants have been disclosed; however, these devices are not disposable, and they are designed to remain in the vagina and release spermicide during the time between menstrual periods. Because of this length of use, they may develop problems with infection, odor, or discomfort, and they are less suited for women who engage in sexual intercourse infrequently.

These and other defects in prior art devices are now overcome by practice of the present invention.

SUMMARY OF THE INVENTION

The above disadvantages of the prior art are overcome by practice of the present invention which is a disposable vaginal device, optionally with a controlled release of a drug. The device acts as a physical barrier to most sperm, any incorporated spermicide increases contraceptive efficacy and acceptability, and the ingredients provide the required surface lubricant for ease of insertion.

It is understood that while the term device is used herein, the present invention is also applicable to other intra-vaginal contraceptive barriers, such as the cervical cap, vimule and vault cap. It is also understood that while spermicides are the preferred biologically active agents delivered to the vagina, other agents such as antimicrobials or antifungals could also be released from the device disclosed herein.

The intra-vaginal device of the present invention includes agarose, a processed agar, in an amount of about 0.1% to about 4% by weight/weight of solution which is saline; a quantity sufficient of saline solution preferably in the amount of about 9% by weight sodium chloride in water; high molecular weight (M.W. of about 100,000 Daltons to about 1,000,000 Daltons) glycosaminoglycans in an amount of about 0.1% to about 20% by weight; collagen in an amount of about 0.1% to about 20% by weight; and fibrin in an amount of about 0.1% to about 20% by weight.

Additionally, the present composition includes from about 1% to about 10% by weight of agarase, a bacterial enzyme which degrades agar and agarose; polysaccharideases use to degrade glycoaminolglycans and carbohydrates generally; collagenase which degrades collagen; and protease which degrades proteins such as fibrin. The enzymes may be isolated from bacteria. Alternatively, the genes for these enzymes may be isolated. Then, they or other natural sources can be prepared from genetically engineered sources. The range of the enzyme is normally present in an amount of about 0.001% to about 10% by weight.

The present device usefully serves as a contraceptive device and system using tested and accepted materials which inhibit sperm motility and fertilizing capacity at low concentration.

The present device also serves as a drub delivery system using a hydrophilic polymer which presently appears to eliminate the possibility of contraction of toxic shock syndrome. The amount of drug content may range from about 0.001% to about 10% by weight.

DETAILED DESCRIPTION OF THE PREFERRED EMBODIMENT

The present invention encompasses disposable devices whose construction allows them to be positioned within the vagina such as to block access of the sperm to the cervix and provide controlled release of a spermicide or other biologically active agents by diffusion from the present system.

As seen in FIGS. 1-4, the preferred embodiment of the present invention is that of a modified cup 10 constructed using the hydrophilic formulation of the present composition 12. The diaphragm is preferably composed of a biologically compatible material that has been blended homogeneously, and preferably with, for example, a spermicide, such as Nonoxynol-9. The spermicide migrates to the surface of the device by diffusion, and is released into the vagina by a controlled rate upon contact with the vaginal fluid.

The spermicide may be incorporated into either the entire portion of the device, system or laminate thereof, if desired. Thus, either a homogeneous blend of the present formulation is prepared, alternatively the device includes a layer of active material, or the active material may be compartmentized as desired. Here a homogeneous blend is preferred.

Figure 1:
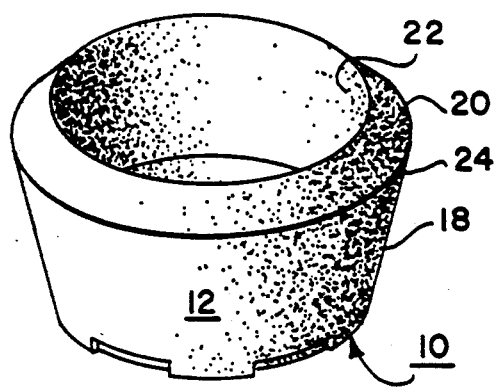
FIG. 1 is a top perspective view of the intra-vaginal device of the present invention.
Figure 2:
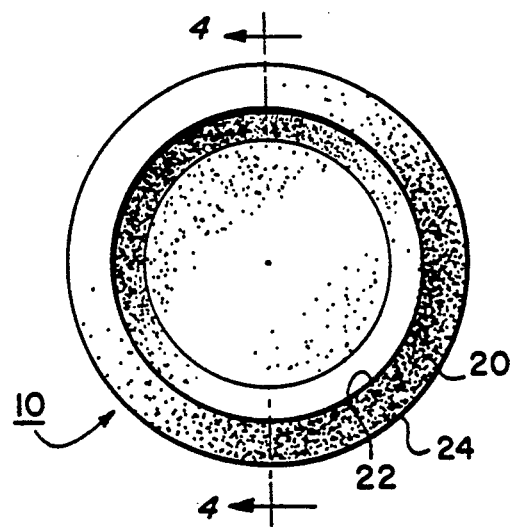
FIG. 2 is a top elevational view thereof.
Figure 3:
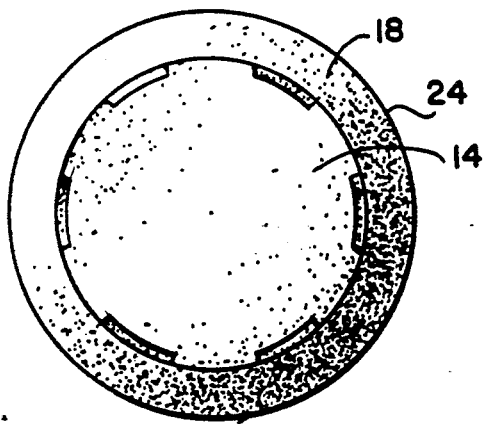
FIG. 3 is a bottom elevational view of the intra-vaginal device of the present invention which illustrates pictorially insertion of the device or system in the vagina.

FIG. 1 illustrates the intra-vaginal device 10 formed of a composition 12, and configured with a base 14 having processing ridges 16 disposed thereon. The circular walls 18 uniformly enlarge from the base 14 at an angle of about 3 to about 10 degrees from the horizontal base. Finally, the upper rim surface 20 is illustrated slightly beveled from the interior wall 22 to the exterior wall 24. Throughout the description of this invention, similar elements are identified by like numerals in the several views.

Figure 4:
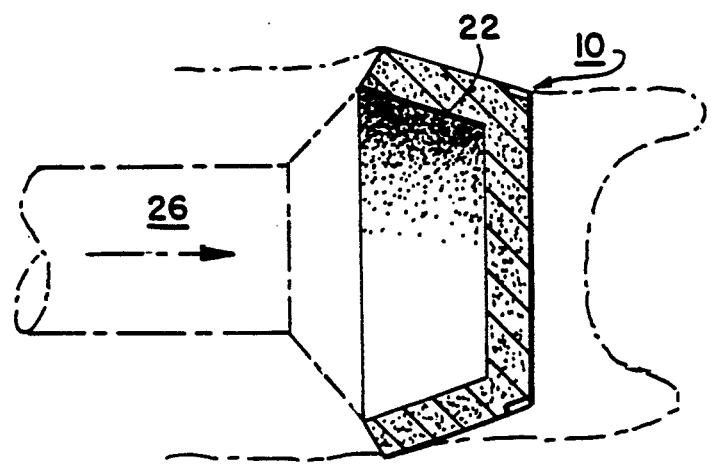
FIG. 4 is a view of the intravaginal device being inserted within the vaginal cavity.

Finally, FIG. 4 pictorially illustrates device 10 being inserted within the vaginal cavity using applicator 26.

In practice of the present invention, the present intra-vaginal device is self-inserted into the vagina. Upon insertion and subsequent contact with the fluids of the vagina, the device, since it is in the gel state, swells within about 2-3 minutes and thereby blocks the cervix by a close association with the walls of the vagina. Once the device swells in place, there is minimal shifting movement or possibility of dislodgement. The device slowly dissolves as a gel-sol over a period of up to about 24 hours, during which time it can be used to controllably release a drug or combinations of drugs over a sustained period of time during the dissolving period. Thus once the present device is inserted, the user does not have to be concerned about removal. Once dissolved, the small amount of residue drains out of the vagina with virtually no discomfort. However, while the device is in place, it blocks the cervix and prevents passage of sperm. When used as a drug delivery system by inclusion of a spermicide, germicide or virucide, the included drug is controllably released over a sustained period of time. Anti-microbials as well as antifungals may be suitably released with the present system, if desired.

Because of the nature and composition of the present device, there is not known contra-indication for toxic shock syndrome.

At the time of insertion, the present device or system is in the solid state. In about 2-3 minutes after insertion, the device, with or without drugs contained therein, contacts the vaginal fluids. During the dissolving stage, the device becomes a gel-sol (liquid colloidal solution) preventing sperm passage into the cervical mucous, while any spermicidal drub present kills the sperm in the vagina. The gel-sol remains in the vagina for up to about 24 hours during which time any remaining sperm is most likely killed. The residue then drains out of the vagina with the sperm and seminal fluid.

The size of the intra-vaginal device of the present invention is standardized. One size is suitable for use. Accurate self-applied positioning is accomplished by using a tampon-like insertion applicator. Once the intra-vaginal device is positioned in place, vaginal fluids cause it to cover and block the cervix by adhering to the vaginal walls.

Because the present devices are fabricated from inexpensive materials, they may be manufactured in mass quantities at a low cost by standard methods, such as molding and casting. As a result of their low cost, devices and systems of the present invention can be made available to a large segment of the population.

Spermicide

A wide variety of spermicides may be used for the present invention to kill, immobilize or otherwise render sperm cells inactive in the vagina. The most preferred spermicide for use in the device of the present invention is Nonoxynol-9, nonylphenoxypolyethoxyethanol, which is currently the most widely used spermicide in vaginal preparations in the United States. Other spermicides which can be used are, for example, p-diisobutylphernoxypolyethanol(Octoxynol), p-methanylphenyl polyoxyethylene (8.8) ether (Menfegol), dodecamethylene glycol monolureate, and sodium lauryl sulfate, although any compatible, water-soluble spermicide may be used. Nonoxynol-9 is preferred because it is considered safe and effective. GAF Corporation and Rohm & Haas Company are examples of suppliers of Nonoxynol-9. There are also other manufacturers of the spermicide.

The amount of spermicide contained in the present system of this invention may vary in accordance with their rate of release from the device and their spermicidal efficacy. In the preferred embodiment of this invention which includes Nonoxynol-9 spermicide, and polyethylene glycol, the amount of Nonoxynol-9 used may vary from about 3 to about 30% by weight based on the total weight of the device, with the preferred amount in the range of from about 2% to about 15% by weight.

Based on the amount of Nonoxynol-9 used in vaginal formulations of the prior art and on the estimated concentration of Nonoxynol-9 necessary to immobilize sperm in vaginal fluid, it is desired that devices of the present system release approximately 40 mg. of Nonoxylnol-9 within about 8 hours following insertion of the device into the vagina. Devices of this invention containing approximately 10% by weight of Nonoxynol-9 are found to release the aforementioned desired amount of Nonoxynol-9.

The present device includes the advantages of standardized diaphragm, cervical cap and contraceptive sponges without virtually any of the known disadvantages thereof.

Drug Delivery System

The present intra-vaginal device usefully includes drug additions and thereby usefully serves as a drug delivery system for controllably releasing drugs into the body by means of the vagina. Typically, vaginal drugs such as miconazole, acyclovie, clotrimazole, ticonazole, hormones, metronizazole, sulfas, and nystatin may be incorporated within the intra-vaginal device in suitable amounts for sustained release over a fixed period of time. Specifically suitable drugs which may be used include sulfabenzamide, sulfacetamide, sulfacytine, sulfatriazole and the like. Benzetimine, a non-steriod anti-inflammatory drug, and alpha-lactalbumin, a protein found in milk may also be included if desired. Monoclonal antibodies such as those useful against cell surface components or against pathogenic organisms such as the human-immuno-deficiency (HIV) family of viruses, may be incorporated into the device of the present invention for ultimate intravaginal release. Thus, the present device is usefully employed as a drug carrier for spermicides, germicides, and virucides. Combinations of these materials in safe and effective amounts may be used as desired. Typically the range of drug additives may be in the amount of about 0.001% to about 10.0% by weight.

The present device may include carrageenan, as either iota or kappa forms, in the amount of about 0.1% to about 20% by weight. Also, locust bean gum may be added in an amount from about 0.1% to about 20% by weight, as may glycerin in an amount from about 0.1% to about 20% by weight.

Various ions may be present in the device of this invention such as sodium ions, chloride ions, phosphate ions, potassium ions and calcium ions in an amount from near zero to about 10 grams per liter.

In preparation of the original gel, polymer solids, including ions, will be mixed in dry form. Water will be added to the proper concentration, and the mixture will be heated to the appropriate temperature of solution. Heating will probably be accomplished by submerging vessels containing the mixture into water or jacketed vessels held at constant temperature. After heating, the solution will either then be poured into molds and cooled to gelatinous temperature, or it will be transferred into another water bath of cooler temperature and other ingredients, such as heat labile enzymes are added. The solution will then be poured into molds and cooled. It is possible that after pouring the solution into the mold, another part of the mold can be closed onto the solution and thereby creating the three dimensional shape of the gel.

It is also possible that the device of the present invention will be blended into laminar form, that is a solution of one composition will be poured into the mold and allowed to begin to gel, at which time another solution of different composition will be poured onto the first gelling solution, and both solutions allowed to gel completely. In this case one has a combination gel.

Also, it is possible to prepare the present device such that it will be gelled and then an ingredient, such as an enzyme, will be injected into the gel.

The device will the be removed from the mold simply by opening the mold into two mating sections, or by injecting air between the gel and the mold, thereby forcing the molded device, now as a gel, from the mold.

EXAMPLE 1

This example demonstrated how drugs incorporated into the device are released when it serves as a drug delivery system. Mannose is equivalent in this case to most any conventional drug to be released from the present device with a molecular weight less than about 5000 Daltons. This includes nearly all drugs listed in the present specification with the possible exception of alpha-lactalbumin and monoclonal antibodies. This protein is expected to be released at an equivalent rate to bovine serum albumin release.

A 12 ml. gel is cast of 3% agarose in phosphated-buffered saline (PBS) which includes 12 mg. of bovine serum albumin and 10 mg. of mannose, some of which was radioactively labeled with tritium. The gel was removed from the mold and placed into a beaker containing 100 ml. PBS maintained at room temperature and gently stirred. At various times, 1 ml. of the PBS solution was removed and the mannose and protein content was determined from the removed solution. After 24 hours, essentially all of the mannose and protein were released from the device. It is found that after about 30 minutes, about 50% of the mannose is released due to its small molecular size, while only about 15% of the protein is found to be released. This demonstrates the different rates of diffusion and therefore different rates of release of small molecular weight drugs and drugs of large molecular weight (protein).

EXAMPLE A

The examples listed below describe several formulations utilizing different structural components (agarose, collagen, carrageenan, hyaluronic acid, locust bean gum) as well as different active ingredients (spermicides and antibacterials). The components which are used in each example are to be mixed according to the following protocol:

A solution of phosphate buffered saline (0.15M NaCl, 0.5 mM $NaH_2PO_4$, pH 6.8) is prepared and a volume of 100 ml is transferred to a flask which is partially immersed in a water bath at 60° C. The specified amount of powdered agarose with a gelling temperature of 35° C. to 38° C. is added to the saline and stirred until completely dissolved and no bubbles are present. Additional components (collagen, hyaluronic acid, locust bean gum, carrageenan, glycerin) are added while the solution is at 60° C. and stirred until dissolved.

The flask is then transferred to a water bath at 40° C. and cooled to this temperature. The specified amount of nonoxynol-9 is then added and stirred until it is in solution. Additional components which may be heat sensitive (agarase, alpha-lactalbumin, monoclonal antibodies and the like) as well as anti-bacterial agents (sulfa-benzamide, sulfatriazole, benzetimine) should be added at 40° C. and stirred until dissolved.

Non-miscible chemicals such as petrolatum are introduced by homogenization with a motor driven homogenizer at 40° C. to form an emulsion.

The final mixture is then poured into molds and cooled to 25° C. which causes the mixture to gel. The mold is then deformed and the formed device is removed.

EXAMPLE 2

The procedure of Example A is repeated except that the following ingredients in amounts indicated are combined, all parts are given by weight. Saline is prepared by a solution of 0.15M NaCl, 0.5 mM $NaH_2PO_4$ at a pH 6.8.

| Ingredients | Parts by Weight |
| --- | --- |
| Saline | 92.0 |
| Agarose | 3.0 |
| Nonoxynol-9 | 5.0 |

EXAMPLE 3

The procedure of Example 2 is repeated except that the following ingredients in amounts indicated are combined, all parts are given by weight:

| Ingredient | Parts by Weight |
| --- | --- |
| Saline | 90.0 |
| Agarose | 3.0 |
| Collagen (bovine) | 1.0 |

| Ingredient | Parts by Weight |
|---|---|
| Hyaluronic Acid | 1.0 |
| Nonoxynol-9 | 5.0 |

EXAMPLE 4

The procedure of Example 2 is repeated except that the following ingredients in amounts indicated are combined, all parts are given by weight:

| Ingredients | Parts by Weight |
|---|---|
| Saline | 91.0 |
| Agarose | 1.0 |
| Carageenan | 2.0 |
| Locust Bean Gum | 1.0 |
| Nonoxynol-9 | 5.0 |

EXAMPLE 5

The procedure of Example 2 is repeated except that the following ingredients in amounts indicated are combined, all parts are given by weight:

| Ingredient | Parts by Weight |
|---|---|
| Saline | 90.9 |
| Agarose | 3.0 |
| Agarase | 0.1 |
| Fibrin | 1.0 |
| Nonoxynol-9 | 5.0 |

EXAMPLE 6

The procedure of Example 2 is repeated except that the following ingredients in amounts indicated are combined, all parts are given by weight:

| Ingredient | Parts by Weight |
|---|---|
| Saline | 83.5 |
| Agarose | 1.0 |
| Glycerine | 10.0 |
| Petrolatum | 0.5 |
| Nonoxynol-9 | 5.0 |

EXAMPLE 7

The procedure of Example 2 is repeated except that the following ingredients in amounts indicated are combined, all parts are given by weight:

| Ingredient | Parts by Weight |
|---|---|
| Saline | 91.0 |
| Collagen | 2.0 |
| Carageenan | 1.0 |
| Nonoxynol-9 | 5.0 |

The procedure described for the preceding Examples 2-7 illustrate practice of the present invention using spermicides.

EXAMPLE 8

The procedure of Example 2 is repeated except that the following ingredients in amounts indicated are combined, all parts are given by weight:

| Ingredient | Parts by Weight |
|---|---|
| Saline | 89.9 |
| Agarose | 3.0 |
| Collagen (bovine) | 1.0 |
| Hyaluronic Acid | 1.0 |
| Nonoxynol-9 | 5.0 |
| Sulfacetamide | 0.1 |

EXAMPLE 9

The procedure of Example 2 is repeated except that the following ingredients in amounts indicated are combined, all parts are given by weight:

| Ingredient | Parts by Weight |
|---|---|
| Saline | 90.9 |
| Agarose | 1.0 |
| Carageenan | 2.0 |
| Locust Bean Gum | 1.0 |
| Nonoxynol-9 | 5.0 |
| Sulfatriazole | 0.1 |

EXAMPLE 10

The procedure of Example 2 is repeated except that the following ingredients in amounts indicated are combined, all parts are given by weight:

| Ingredient | Parts by Weight |
|---|---|
| Saline | 90.4 |
| Agarose | 3.0 |
| Agarase | 0.1 |
| Fibrin | 1.0 |
| Nonoxynol-9 | 5.0 |
| Benzetimine | 0.5 |

EXAMPLE 11

The procedure of Example 2 is repeated except that the following ingredients in amounts indicated are combined, all parts are given by weight:

| Ingredient | Parts by Weight |
|---|---|
| Saline | 83.4 |
| Collagen | 2.0 |
| Agarose | 1.0 |
| Glycerine | 10.0 |
| Petrolatum | 0.5 |
| Nonoxynol-9 | 5.0 |
| Sufabenzamide | 0.1 |

EXAMPLE 12

The procedure of Example 2 is repeated except that the following ingredients in amounts indicated are combined, all parts are given by weight:

| Ingredient | Parts by Weight |
|---|---|
| Saline | 86.0 |
| Collagen | 2.0 |
| Agarose | 1.0 |
| Carageenan | 1.0 |
| Nonoxynol-9 | 5.0 |
| Alpha-lactalbumin | 5.0 |

EXAMPLE 13

The procedure of Example 2 is repeated except that the following ingredients in amounts indicated are combined, all parts are given by weight:

| Ingredients | Parts by Weight |
| --- | --- |
| Saline | 91.0 |
| Agarose | 3.0 |
| Nonxynol-9 | 5.0 |
| Monoclonal Antibody | 1.0 |

The procedure described for the preceding Examples 8–13 illustrate practice of the present invention for spermicides and bacteriocides.

It will be readily apparent to those skilled in the art that numerous modifications and additions may be made to both the present invention, the disclosed device, and the related system without departing from the invention which is disclosed.

What is claimed is:

1. A solidified gel composition suitable for use as an intra-vaginal insert, capable of dissolution or disintegration in the presence of vaginal fluids and consisting essentially of an aqueous saline solution containing a gelling agent dissolved or dispersed therein, said gelling agent being selected from the group consisting of agarose or agar, glycosaminoglycan, collagen, carageen or carageenan, locust bean gum, fibrin and glycerine, and an enzyme selected from the group consisting of protease, agarase, collagenase and saccharidase, said gelling agent and said enzyme being present in said composition in minor amounts totaling less than fifty percent by weight.

2. A composition in accordance with claim 1 wherein said composition additionally contains an effective amount of an additive selected from the group consisting of an antimicrobial, an antifungal, a virucide and a spermicide.

* * * * *

UNITED STATES PATENT AND TRADEMARK OFFICE
CERTIFICATE OF CORRECTION

PATENT NO.  : 5,069,906
DATED       : December 3, 1991
INVENTOR(S) : Robert S. Cohen, et al.

It is certified that error appears in the above-identified patent and that said Letters Patent is hereby corrected as shown below:

On the title page, item [63] should read--

[63]　　　　Related U.S. Application

Continuation of Ser. No. 257,156, Oct. 14, 1988, Pat. No. 4,983,393, which is a continuation of Ser. No. 75,898, Jul. 21, 1987, abandoned. --.

Column 1, line 6, "057,898" should read—075,898--.

Signed and Sealed this

Fifteenth Day of August, 2000

Attest:

Q. TODD DICKINSON

*Attesting Officer*　　　　*Director of Patents and Trademarks*